(12) United States Patent
Feuerlein et al.

(10) Patent No.: US 9,414,798 B2
(45) Date of Patent: Aug. 16, 2016

(54) SYSTEM AND METHOD FOR AUTOMATIC TRIGGER-ROI DETECTION AND MONITORING DURING BOLUS TRACKING

(75) Inventors: Ute Feuerlein, Erlangen (DE); Arun Krishnan, Exton, PA (US); Xiang Sean Zhou, Exton, PA (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 649 days.

(21) Appl. No.: 12/729,274

(22) Filed: Mar. 23, 2010

(65) Prior Publication Data

US 2010/0249582 A1    Sep. 30, 2010

Related U.S. Application Data

(60) Provisional application No. 61/163,233, filed on Mar. 25, 2009.

(51) Int. Cl.
*A61B 6/00* (2006.01)
*A61B 6/03* (2006.01)
*A61B 5/00* (2006.01)

(52) U.S. Cl.
CPC .............. *A61B 6/504* (2013.01); *A61B 6/032* (2013.01); *A61B 6/469* (2013.01); *A61B 6/481* (2013.01); *A61B 6/488* (2013.01); *A61B 5/7285* (2013.01); *A61B 6/541* (2013.01)

(58) Field of Classification Search
CPC ............................ A61B 6/481; A61B 6/469
USPC ................................................ 600/407, 420
See application file for complete search history.

(56) References Cited

U.S. PATENT DOCUMENTS

| | | | |
|---|---|---|---|
| 4,263,916 A * | 4/1981 | Brooks et al. | 600/431 |
| 5,602,891 A * | 2/1997 | Pearlman | 378/62 |
| 7,054,406 B2 * | 5/2006 | Ikeda et al. | 378/8 |
| 7,145,982 B2 | 12/2006 | Ikeda et al. | |
| 2002/0107438 A1 | 8/2002 | Liu et al. | |
| 2002/0151780 A1 | 10/2002 | Klotz | |
| 2003/0210820 A1 * | 11/2003 | Lachner et al. | 382/209 |
| 2005/0020903 A1 * | 1/2005 | Krishnan | G06F 19/345 600/407 |
| 2006/0247518 A1 | 11/2006 | Boing et al. | |
| 2007/0062251 A1 * | 3/2007 | Anex | 73/1.36 |
| 2007/0238956 A1 * | 10/2007 | Haras et al. | 600/407 |
| 2007/0258558 A1 | 11/2007 | Nishide et al. | |

(Continued)

FOREIGN PATENT DOCUMENTS

CN           101185591 A       5/2008

OTHER PUBLICATIONS

International Search Report of Application Serial No. PCT/US2010/028605 dated Jul. 1, 2010.

(Continued)

*Primary Examiner* — Rochelle Turchen
(74) *Attorney, Agent, or Firm* — Peter Kendall (57) ABSTRACT

A method for bolus tracking includes acquiring one or more baseline images. One or more trigger regions are automatically established within the baseline images. A bolus is administered. The automatically established trigger regions are monitored for bolus arrival at the one or more trigger regions. Bolus arrival at a volume of interest is forecasted based on the bolus arrival at the one or more trigger regions. A diagnostic scan of the volume of interest is acquired at the forecasted time.

26 Claims, 4 Drawing Sheets

(56) References Cited

U.S. PATENT DOCUMENTS

2008/0097196 A1* 4/2008 Licato et al. ............. 600/431
2008/0253634 A1   10/2008 Hay et al.
2011/0060755 A1* 3/2011 Mollus et al. ............. 707/769

OTHER PUBLICATIONS

Search report of Chinese Patent Application No. 201080013356.9.
Office action dated Oct. 9, 2013 in Chinese Application No. 2010080013356.9 (English translation attached).

\* cited by examiner

FIG. 4

SYSTEM AND METHOD FOR AUTOMATIC TRIGGER-ROI DETECTION AND MONITORING DURING BOLUS TRACKING

CROSS-REFERENCE TO RELATED APPLICATION

The present application is based on provisional application Ser. No. 61/163,233, filed Mar. 25, 2009, the entire contents of which are herein incorporated by reference.

BACKGROUND OF THE INVENTION

1. Technical Field

The present disclosure relates to bolus tracking and, more specifically, to a system and method for automatic trigger-ROI detection and monitoring during bolus tracking.

2. Discussion of Related Art

Bolus tracking is used as part of some medical imaging procedures such as computed tomography (CT) angiography or magnetic resonance imaging (MRI) angiography for visualizing blood vessels and organs within the human body. During bolus tracking for CT angiography, a quantity of radio-opaque contrast media known as a bolus is injected into a patient's circulatory system via a peripheral intravenous cannula. The radio-opaque contrast media may then be imaged using a computed tomography (CT) scanner and the volume of the bolus may be observed. A triggering region of interest (trigger-ROI) is defined within the body and the CT scanner may be used to detect when the contrast arrives at the trigger-ROI. This is achieved by using a series of dynamic low-dose monitoring scans. Then, after sufficient time elapses to allow the bolus to travel from the trigger-ROI to a predetermined volume of interest (VOI), the predetermined VOI is imaged. By examining the appearance and volume of the bolus within the VOI, significant diagnostic information pertaining to the visualized blood vessels may be obtained.

Bolus tracking is used to image blood flow through arteries such as the carotid arteries, coronary artery, through highly vascularized organs such as the liver, or other regions through which blood flows.

Generally, the location of the monitoring scan and the placement of the trigger-ROI are defined manually by the technician performing the study. The contrast arrival is detected either visually by the technician or with the assistance of software which alerts the technician when the intensity inside the ROI has increased by more than a pre-set threshold.

SUMMARY

A method for bolus tracking includes acquiring one or more baseline images. One or more trigger regions are automatically established within the baseline images. A bolus is administered. The automatically established trigger regions are monitored for bolus arrival at the one or more trigger regions. Bolus arrival at a volume of interest is forecasted based on the bolus arrival at the one or more trigger regions. A diagnostic scan of the volume of interest is acquired at the forecasted time.

Acquisition of the baseline image may include acquiring a scout image, automatically detecting a monitoring line within the scout image, and acquiring the baseline image at an image slice determined by the location of the automatically detected monitoring line within the scout image.

Automatic establishment of the one or more trigger regions within the baseline image may include automatically determining a shape, size, and location of the one or more trigger regions. One or more trigger regions may be automatically established based on anatomical context. Monitoring the automatically established trigger regions for bolus arrival at the one or more trigger regions may include performing motion compensation to correct for patient motion within the baseline image. Motion compensation may include repositioning a field of image acquisition around each trigger region in the event of movement.

The baseline image may be a low-dose CT image, the bolus may include a radio-opaque contrast medium, and the diagnostic scan may be a high-resolution CT image.

An injection site for administering the bolus may be automatically selected.

One or more anatomical landmarks may be automatically identified within the baseline image and monitoring the automatically established trigger regions for bolus arrival at the one or more trigger regions may include tracking the trigger regions and the anatomical landmarks and registering the trigger regions to an anatomical coordinate system referencing the tracked anatomical landmarks.

One or more trigger regions may include a plurality of trigger regions. Each of the one or more trigger regions may be automatically assigned a confidence score. The confidence scores of the one or more trigger regions may be used in combination with bolus arrival at the trigger regions in forecasting bolus arrival at the volume of interest. Forecasting bolus arrival at a volume of interest based on the bolus arrival at the one or more trigger regions may include using bolus arrival information from only a $k^{th}$ trigger region. Here, k may be a predetermined or selected positive integer.

A method for bolus tracking includes acquiring a scout image, automatically detecting a monitoring line within the scout image, acquiring a baseline image at a location determined by the location of the automatically detected monitoring line within the scout image, acquiring a baseline image, automatically establishing a plurality of trigger regions within the baseline image, administering a bolus, monitoring the automatically established trigger regions for bolus arrival at the one or more trigger regions, forecasting bolus arrival at a volume of interest based on the bolus arrival at the one or more trigger regions, and acquiring a diagnostic scan of the volume of interest at the forecasted time.

Each of the one or more trigger regions may be automatically assigned a confidence score and the confidence scores may be used in combination with bolus arrival at the trigger regions in forecasting bolus arrival at the volume of interest.

Monitoring the automatically established trigger regions for bolus arrival at the one or more trigger regions may include performing motion compensation to correct for patient motion within the baseline image. The motion compensation may include repositioning a field of image acquisition around each trigger region in the event of movement.

A computer system includes a processor and a non-transitory, tangible, program storage medium, readable by the computer system, embodying a program of instructions executable by the processor to perform method steps for bolus tracking. The method includes acquiring a scout image, automatically detecting a monitoring line within the scout image, acquiring a baseline image at a location determined by the location of the automatically detected monitoring line within the scout image, acquiring a baseline image, automatically establishing one or more trigger regions within the baseline image, administering a bolus, monitoring the automatically established trigger regions for bolus arrival at the one or more trigger regions, forecasting bolus arrival at a volume of interest based on the bolus arrival at the one or more trigger regions, and acquiring a diagnostic scan of the volume of interest at the forecasted time.

Monitoring the automatically established trigger regions for bolus arrival at the one or more trigger regions includes performing motion compensation to correct for patient motion within the baseline image.

One or more anatomical landmarks may be automatically identified within the baseline image and monitoring the automatically established trigger regions for bolus arrival at the one or more trigger regions may include tracking the trigger regions and the anatomical landmarks and registering the trigger regions to an anatomical coordinate system referencing the tracked anatomical landmarks.

Each of the one or more trigger regions may be automatically assigned a confidence score.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention provide a system and method for performing bolus tracking wherein one or more triggering-ROIs may be automatically determined. Advanced triggering criteria may then be used to analyze the bolus volume data collected at each of the one or more triggering-ROIs and to use this information to establish highly reliable triggering criteria. Upon the commencement of VOI imaging, exemplary embodiments of the present invention may track and correct for motion within the VOI such as breathing motion, cardiac motion, and patient motion so that the image acquisition plane may actively correct for the tracked motion and the image acquisition plane can maintain a fixed position relative to the anatomy being imaged, even in the presence of motion. Exemplary embodiments of the present invention may also correct for such motion within the baseline images that are used to track trigger regions used to predict bolus arrival in the VOI.

Figure 1:
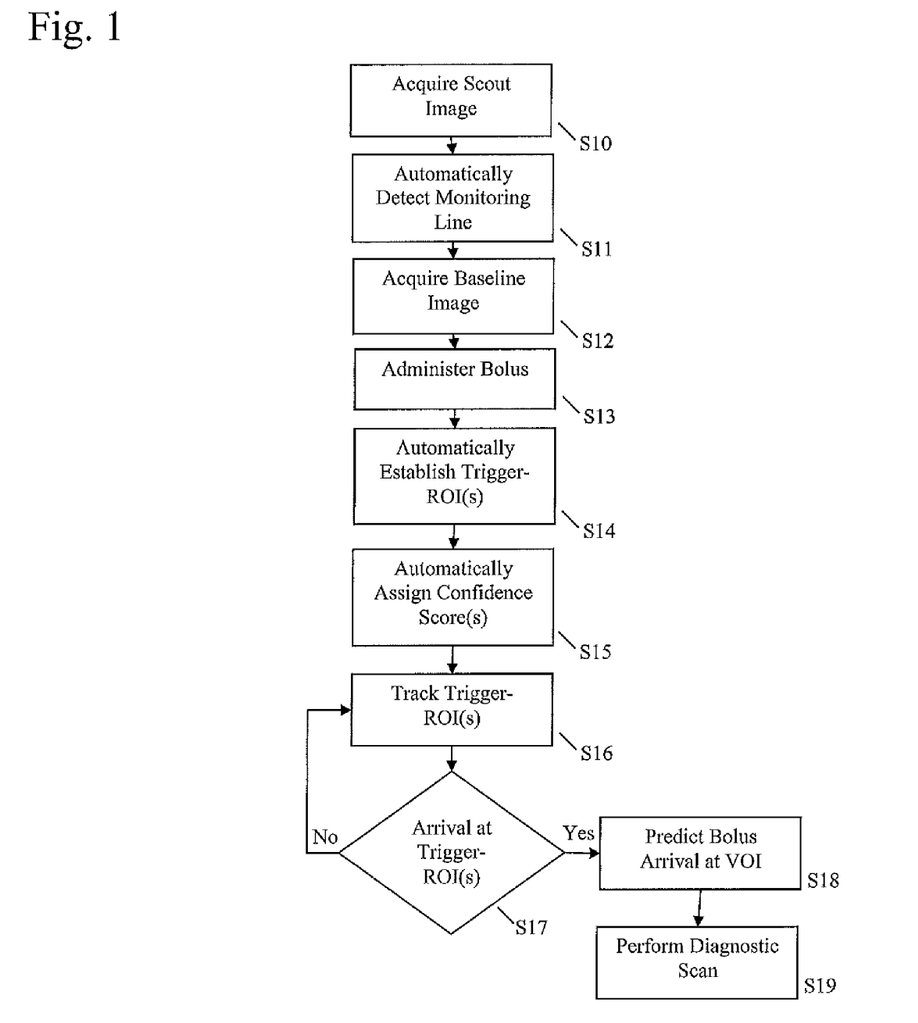
FIG. 1 is a flow chart illustrating an approach for performing bolus tracking with automatic triggering-ROI selection according to an exemplary embodiment of the present invention.

FIG. 1 is a flow chart illustrating an approach for performing bolus tracking with automatic triggering-ROI selection according to an exemplary embodiment of the present invention. First, a scout image may be acquired (Step S10). A scout image may be a preliminary CT scan of the subject that encompasses a large enough region to include the volume of interest (VOI) and surrounding locations that may be used as triggering regions of interest (trigger-ROIs). For example, the scout image may encompass substantially the entire body. The scout image may be acquired relatively quickly and may have a reduced resolution. The scout image may be a 2D topogram image. Acquisition of the scout image may be optionally omitted.

Next, a monitoring line may be automatically detected within the acquired scout image (Step S11). The monitoring line may define an imaging plane for subsequent acquisition of monitoring or baseline image(s). The image plane defined by the monitoring line may serve as a plane within which one or more triggering-ROIs may be established. Thus, the monitoring line may be used to establish a particular image slice that will be of interest in the process of bolus tracking. Automatic establishment of the monitoring line may be performed using anatomical context found within the scout image. Accordingly, knowledge as to the particular anatomical region being studied may be used to detect a suitable monitoring line after quick segmentation is performed within the scout image to identify pertinent anatomical landmarks. The monitoring line may be tilted to achieve optimal (e.g., more stable) trigger-ROIs, for example, when the line is perpendicular to a blood vessel, a trigger-ROI placed inside the vessel would be more stable to out-of-plane motion of the baseline images due to patient motion. The step of automatically detecting the monitoring line from the scout image may be optionally omitted, for example, in cases where the acquisition of the scout image has been omitted.

Figure 3:
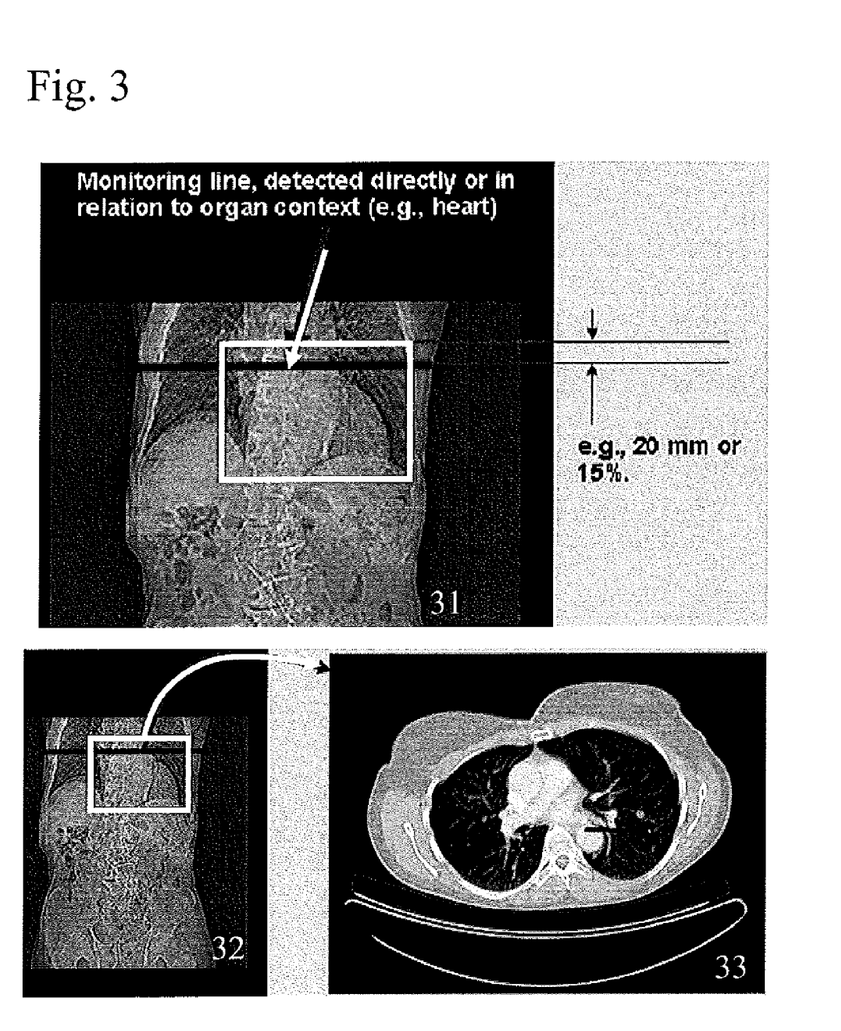
FIG. 3 illustrates automatic detection of the monitoring line for establishing slice location of the low-dose baseline images according to an exemplary embodiment of the present invention.

FIG. 3 illustrates automatic detection of the monitoring line for establishing slice location of the low-dose baseline image(s) according to an exemplary embodiment of the present invention. As can be seen here, the context of the image may be identified either directly or in relation to organ context (for example, the heart). The white box of images 31 and 32 represent the organ context which may be identified (for example, either automatically or manually) and based on the identified context, the monitoring line (shown as the dark horizontal line of images 31 and 32) may be automatically detected. Based on the automatically detected monitoring line, an appropriately oriented baseline image 33 may be acquired.

Next, one or more baseline images may be acquired (Step S12). The baseline image may be a low-dose CT scan taken along the image plane defined by the monitoring line. For example, the monitoring line within the scout image may be registered to the CT acquisition coordinate such that image data of a particular slice corresponding to the plane of the baseline image is acquired. The baseline image may be just one spatial slice (but acquired multiple times over time) or may cover a narrow spatial field of view and may contain the volume of interest (VOI) and a surrounding neighborhood. For example, the baseline image may be an axial view of the pulmonary artery trunk bifurcation. The baseline image may be re-acquired at predetermined time intervals so as to capture progress of the bolus. Accordingly, in this step, acquisition of the baseline image may be started and acquisition of the baseline image may continue. The bolus of radio-opaque contrast agent may be administered (Step S13) at substantially the same time as the baseline image is acquired. Accordingly administration of the contrast agent may occur either before, during, or immediately after the acquisition of the baseline image. According to some exemplary embodiments of the present invention, acquisition of the baseline image may be started prior to the administration of the bolus in order to acquire at least one baseline image that is guaranteed free of the bolus.

Administration of the bolus may be performed, for example, by injecting the radio-opaque contrast agent into the patient's circulatory system via a peripheral intravenous cannula. The injection site may be user-selected according to the anatomy being studied or exemplary embodiments of the present invention may provide automatic injection site guidance based on the imaging protocol, the scout image, and anatomical context.

Next, one or more trigger-ROIs may be automatically placed within the baseline image (Step S14). Automatic placement of the trigger-ROIs may include making an automatic determination as to the location, shape, and size of the ROIs. These determinations may be made based on knowledge of the anatomical context of the volume of interest (VOI). A lookup table may be used to identify the location, size, and shape of the one or more trigger-ROIs. The lookup table may be used to cross-reference the anatomical description of the VOI with a plurality of trigger-ROIs. For example, where the baseline image is an axial view of the pulmonary trunk bifurcation, a trigger-ROI may be a circle or an ellipse that is automatically located within the ascending or descending aorta, or both.

For example, where the Circle of Willis is the subject of the study, and accordingly, defines the VOI, multiple trigger-ROIs may be placed in the baseline image to ensure coverage of possible triggering regions, which may be, for example, the aorta or carotid and vertebral arteries. According to this example, since the Circle of Willis has multiple blood supply sources, trigger-ROIs may be automatically placed on all the internal cardioids and vertebral arteries such that in the event that one or more of the blood supply sources are obstructed, bolus arrival via the other vessels may still be used to accurately predict contrast arrival in the Circle of Willis.

In automatically determining the trigger-ROIs within the baseline image, the anatomical context of the VOI may either be automatically determined, for example, based on the field of view of the baseline image, or may be manually provided by user input.

As placement of the trigger-ROIs may depend on anatomical context, anatomical context may be determined, for example, by automatically detecting one or more anatomical landmarks within the baseline image. Anatomical landmarks may be identified, for example, using visual pattern detection and recognition techniques.

Each of the one or more trigger-ROIs may be automatically assigned a confidence score (Step S15). The confidence score may represent the level of certainty associated with the ability of the corresponding trigger-ROI to accurately predict the arrival of the bolus within the volume of interest based on the identification of the bolus within the trigger-ROI. Accordingly, where there are multiple trigger-ROIs, each with a corresponding confidence score, an accurate estimate as to when the bolus is to arrive within the VOI may be based on each of the trigger-ROIs, weighted according to its confidence score. For example, if arrival of the bolus at a first trigger-ROI indicates that the bolus should arrive at the VOI at a time $T_1$, with a confidence score of 89%, and the arrival of the bolus at a second trigger-ROI indicates that the bolus should arrive at the VOI at a time $T_2$ with a confidence score of 98%, then exemplary embodiments of the present invention may determine that the bolus should arrive at the VOI at a time $T_3$ that is calculated as a weighted average of $T_1$ and $T_2$ that is weighted in proportion to the confidence score, and as such, in the present example, tends to skew towards time $T_2$.

Alternatively, bolus arrival at the VOI may be perdicted based on a single trigger-ROI having the greatest confidence score.

In addition to or in place of confidence scoring, a reasoning module may be employed to provide a measure of flexibility in the triggering logic that predicts the time of bolus arrival in the VOI based on the one or more trigger-ROI(s). According to the reasoning module, the diagnostic scan at the predicted time of bolus arrival may be triggered by the first trigger-ROI to observe the bolus, the last trigger-ROI to observe the bolus, a $k^{th}$ trigger-ROI to observe the bolus (where k is a predetermined or selected positive integer), or by a combination of input from one or more of the trigger-ROIs. A user may be able to specify which approach is dictated by the reasoning module or a determination may be automatically made based on prior knowledge collected during similar studies.

The confidence score may thus be determined as a level of confidence in the ability of the time of arrival of the bolus within the VOI to be forecasted based on the corresponding trigger-ROI. Confidence scores may be calculated either from predetermined formula or based on computer learning techniques which keep track of how often a particular trigger-ROI is able to accurately forecast bolus arrival. The automatic assignment of confidence score may be an optional feature of exemplary embodiments of the present invention.

The automatically detected one or more trigger-ROIs may then be tracked within the baseline image (Step S16). Tracking of the trigger-ROIs may be used to compensate for motion cause by, for example, cardiac motion, breathing motion, and/or patient motion. Without tracking trigger-ROIs, it may be possible for motion to temporarily or permanently compromise the ability of one or more trigger-ROIs to accurately predict the time of bolus arrival at the VOI. This may happen as motion either places the trigger-ROI partially or completely beyond the location where bolus arrival may be detected or by causing obstruction of a trigger-ROI. Tracking may accordingly serve to reposition or resize the trigger-ROIs in the event that image shifting occurs.

Here, in-plane and/or out-of-plane motion may be automatically modeled, detected and monitored. Observed in-plane and out-of-plane motion in the baseline image may be categorized as either periodic motion, such as breathing motion and cardiac motion, or as spontaneous motion such as patient motion. For the former, automatically detected landmarks, for example, in the heart for cardiac motion and on the diaphragm for breathing motion, may be used to model and predict the observed motion. For the latter, probabilities of various forms of motion may be understood such that when a particular part of the body is imaged, common types of motion may be known in advance and thus may be handled appropriately. For example, when the baseline image corresponds to a high patient motion region such as the neck, re-initialization of ROI detection may be set to occur at a higher frequency as compared to a part of the body that is less likely to experience such motion, such as the torso. For example, ROT detection may occur as few as one time with respect to parts of the body that are known to experience less spontaneous motion while ROI detection for parts of the body that are known to experience greater spontaneous motion may be frequently invoked.

The automatically detected anatomical landmarks may also be tracked, for example, in a similar manner. Moreover, confidence scores may be automatically and/or continuously updated, for example, for trigger-ROIs where motion cannot be adequately compensated for. Trigger-ROIs and landmarks may be tracked either separately or jointly.

In tracking the trigger-ROI(s), rigid and deformable registration and/or motion tracking may be used to further refine the focus on and tracking of the trigger-ROI(s). Accordingly, various registration and motion-tracking techniques may be employed at a local-volume or full-image level.

The one or more trigger-ROIs may then be monitored for the arrival of the bolus therein (Step S17). Monitoring of the trigger-ROIs may include assessing a level of contrast within the trigger-ROI areas and when the level of contrast increase exceeds a predetermined threshold, it may be determined that the bolus has arrived at the trigger-ROIs. As long as it is not determined that the bolus has arrived (No, Step S17), automatic tracking may continue (Step S16). When it is determined that the bolus has arrived (Yes, Step S17) then the arrival of the bolus at the particular trigger-ROI may be used to predict a time of bolus arrival at the VOI (Step S18). As there may be multiple trigger-ROIs, as described above, each trigger ROI may be monitored to determine bolus arrival (Step S17) and accordingly, even when it is determined that the bolus has arrived at one particular trigger-ROT, monitoring may continue at the remaining trigger-ROIs until they respectively determine bolus arrival.

During monitoring of the trigger-ROT(s), false triggers of bolus arrival may occur, for example, when a bony structure, calcification, dense implant, etc. near a vessel wall shifts into the ROI as the result of patient motion as arrival of dense tissue into the field of the trigger-ROI may increase image contrast and/or intensity above the relevant threshold. Accordingly, multiple trigger-ROIs may be monitored at substantially the same time so that such obstructions may be avoided, ROI size and/or shape can be modified, and/or the confidence score can be lowered.

Figure 2:
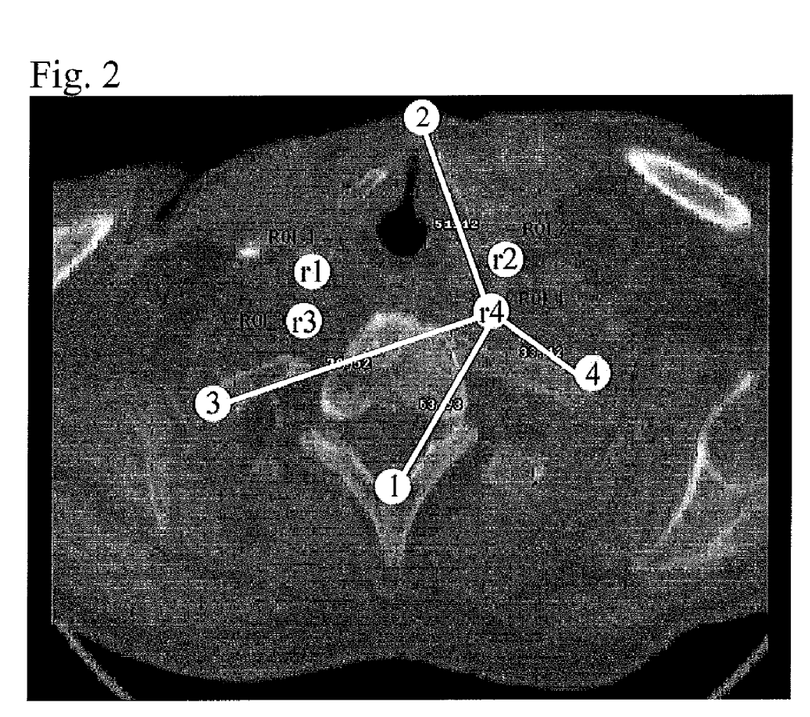
FIG. 2 illustrates an example of an anatomical coordinate system for tracking trigger-ROI(s) according to an exemplary embodiment of the present invention.

Also during monitoring of the trigger-ROI(s), an anatomical coordinate system that is related to patient anatomy, rather than the patient table, may be identified so that trigger-ROIs may be tracked with respect to the anatomical coordinate system instead. By using an anatomical coordinate system, trigger-ROIs may be more accurately monitored with less computational overhead. FIG. 2 illustrates an example of an anatomical coordinate system for tracking trigger ROI(s) according to an exemplary embodiment of the present invention. Here, there are four trigger-ROIs labeled r1, r2, r3 and r4, each appearing within a baseline view including a neck region. Four anatomical landmarks labeled 1, 2, 3, and 4 are also marked on the image. Here, the anatomical landmarks 1-4 form the basis of the anatomical coordinate system, which is shown as the white lines interconnecting the anatomical landmarks 1-4. Each ROI's location and angle relative to the four anatomical landmarks may be detected and tracked. Thus, even in the event of a sudden and substantial shift of position, location of each trigger-ROT may be easily located relative to the anatomical coordinate system anchored by the anatomical landmarks.

A diagnostic scan may be performed at the VOI at the time predicted by the arrival of the bolus at the trigger-ROIs (Step S19). Until that time has arrived, monitoring may continue at all trigger-ROIs that have not yet seen bolus arrival. Thus, it is possible for the predicted time of bolus arrival at the VOI to change somewhat as bolus arrival occurs at additional trigger-ROIs. However, once the diagnostic scan begins, it is no longer necessary to monitor trigger-ROIs that for some reason have failed to register the arrival of the bolus.

The diagnostic scan may be a high-resolution CT scan that may illustrate the flow of the bolus through the volume of interest. The diagnostic scan may, for example, include multiple image volumes that illustrate progression of the bolus though the volume of interest over time.

Exemplary embodiments of the present invention may be applied to other modalities than CT imagery. For example, MRI may be used to acquire one or more of the baseline images and the diagnostic scan. In such a case, a different contrast agent may be used as the bolus. Additionally, still other medical imaging modalities known in the field of nuclear medicine and radiology may be used.

Figure 4:
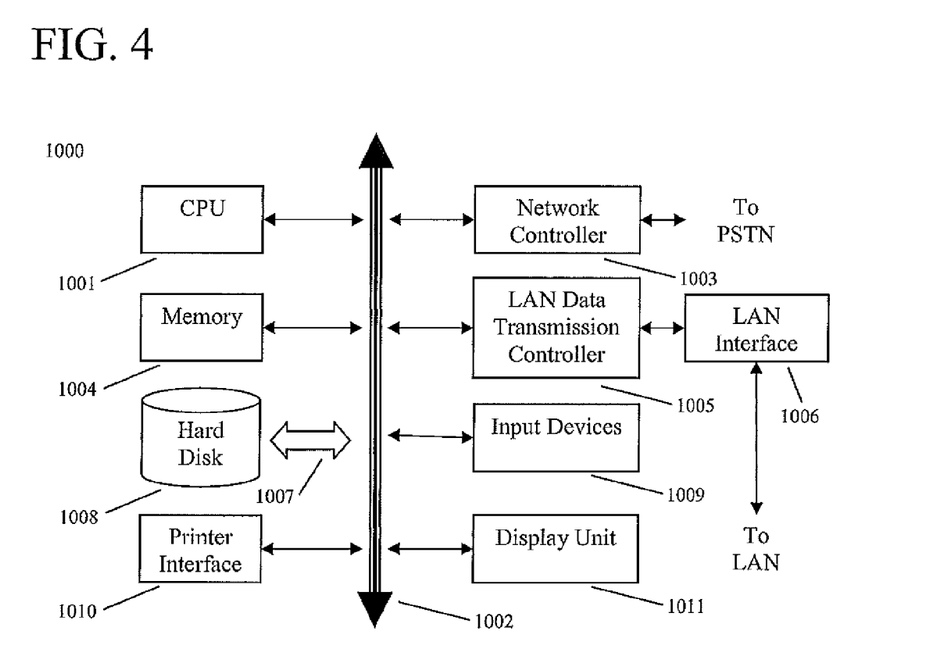
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for bolus tracking, comprising:
    acquiring one or more baseline images;
    automatically establishing trigger regions within each of the one or more baseline images by determining an anatomical context of a volume of interest and automatically cross-referencing the anatomical context to the trigger regions;
    administering a bolus;
    monitoring the automatically established trigger regions for bolus arrival at the trigger regions;
    forecasting first and second bolus arrival times at the volume of interest based on the bolus arrival at first and second of the trigger regions;
    automatically calculating first and second confidence scores corresponding to the first and second of the trigger regions, wherein each of the first and second confidence scores represents a level of certainty associated with an ability of a corresponding trigger region to accurately predict the bolus arrival within the volume of interest based on identification of the bolus within the corresponding trigger region;
    forecasting a third bolus arrival time at the volume of interest based on an average of the first and second bolus arrival times weighted in proportion to the confidence scores; and
    acquiring a diagnostic scan of the volume of interest at the forecasted third bolus arrival time.

2. The method of claim 1, wherein acquisition of the baseline images comprises:
    acquiring a scout image;
    automatically detecting a monitoring line within the scout image; and acquiring the one or more baseline images at an image slice determined by the location of the automatically detected monitoring line within the scout image.

3. The method of claim 1, wherein automatic establishment of the trigger regions within the one or more baseline images includes automatically determining a shape, size, and location of the trigger regions.

4. The method of claim 1, wherein automatic establishment of the trigger regions within the one or more baseline images includes automatically determining the anatomical context by detecting one or more landmarks within the one or more baseline images.

5. The method of claim 4, wherein automatic establishment of the trigger regions within the one or more baseline images includes locating each of the trigger regions inside blood vessels and labeling each of the trigger regions to be indicative of a corresponding anatomical location.

6. The method of claim 5 wherein locating each of the trigger regions inside the blood vessels includes locating each of the trigger regions inside an ascending aorta, aortic arch, descending aorta, abdominal aorta, internal carotid artery, or external carotid artery.

7. The method of claim 1, wherein monitoring the automatically established trigger regions for bolus arrival at the trigger regions includes performing motion compensation to correct for patient motion, respiratory motion, or cardiac motion within the one or more baseline images.

8. The method of claim 7, wherein motion compensation includes repositioning one or more of the trigger regions.

9. The method of claim 1, wherein acquiring the one or more baseline images includes acquiring one or more low-dose CT images, wherein administering the bolus includes administering a radio-opaque contrast medium, and wherein acquiring the diagnostic scan includes acquiring a high-resolution CT scan.

10. The method of claim 1, further comprising automatically selecting an injection site for administering the bolus.

11. The method of claim 1, further comprising automatically identifying one or more anatomical landmarks within the baseline image, and wherein monitoring the automatically established trigger regions for bolus arrival at the trigger regions includes tracking the trigger regions and the anatomical landmarks and registering the trigger regions to an anatomical coordinate system referencing the tracked anatomical landmarks, wherein two of the one or more baseline images are registered to the anatomical coordinate system.

12. The method of claim 11, wherein tracking of the trigger regions relative to the anatomical coordinate system includes changing one or more of the trigger regions in shape, location or size, over time.

13. The method of claim 1, wherein monitoring the automatically established trigger regions for bolus arrival at the trigger regions includes recording image intensity statistics at each of the trigger regions over time, and jointly using the trigger regions and the image intensity statistics to forecast the bolus arrival at the volume of interest.

14. The method of claim 13, wherein recording image intensity statistics at each of the trigger regions over time includes recording a maximal, median, average intensity, or k-th bolus arrival where arrival is defined as an increase of image intensity above a set threshold and k is a predetermined or selected positive integer.

15. The method of claim 1, wherein automatically calculating the first and second confidence scores comprises performing machine learning that keeps track of how often the corresponding trigger region is able to accurately forecast the bolus arrival.

16. The method of claim 15, further comprising automatically and continuously updating the confidence scores of the trigger regions.

17. The method of claim 1, wherein the first trigger region is the trigger region where the bolus first arrives and the second trigger region is the trigger region where the bolus last arrives.

18. The method of claim 1, wherein automatically calculating the first and second confidence scores comprises calculating a pre-determined formula.

19. The method of claim 1, wherein automatically cross-referencing the anatomical context of the volume of interest to the trigger regions includes using a lookup table to cross-reference an anatomical description of the volume of interest to the trigger regions.

20. A method for bolus tracking, comprising:
acquiring a scout image;
automatically detecting a monitoring line within the scout image;
acquiring a baseline image at a location determined by the location of the automatically detected monitoring line within the scout image;
automatically establishing a plurality of trigger regions within the baseline image by determining an anatomical context of a volume of interest and automatically cross-referencing the anatomical context to the trigger regions;
administering a bolus;
monitoring the automatically established trigger regions for bolus arrival at the trigger regions;
forecasting first and second bolus arrival times at the volume of interest based on the bolus arrival at first and second of the trigger regions, and forecasting a third bolus arrival time at the volume of interest based on an average of the first and second bolus arrival times weighted in proportion to confidence scores corresponding to the first and second trigger regions, wherein each of the confidence scores represents a level of certainty associated with an ability of a corresponding trigger region to accurately predict the bolus arrival within the volume of interest based on identification of the bolus within the corresponding trigger region; and
acquiring a diagnostic scan of the volume of interest at the forecasted third bolus arrival time.

21. The method of claim 20, further comprising automatically assigning each of the trigger regions a confidence score.

22. The method of claim 20, wherein monitoring the automatically established trigger regions for bolus arrival at the trigger regions includes performing motion compensation to correct for patient motion within the baseline image, the motion compensation including repositioning one or more of the trigger regions.

23. A computer system comprising:
a processor; and
a non-transitory storage medium, readable by the computer system, embodying a program of instructions executable by the processor to perform method steps for bolus tracking, the method comprising:
acquiring a scout image;
automatically detecting a monitoring line within the scout image;
acquiring a baseline image at a location determined by the location of the automatically detected monitoring line within the scout image;
automatically establishing trigger regions within the baseline image by determining an anatomical context of a volume of interest and automatically cross-referencing the anatomical context to the trigger regions;

administering a bolus;

monitoring the automatically established trigger regions for bolus arrival at the trigger regions;

forecasting first and second bolus arrival times at the volume of interest based on the bolus arrival at first and second of the trigger regions, and forecasting a third bolus arrival time at the volume of interest based on an average of the first and second bolus arrival times weighted in proportion to confidence scores corresponding to the first and second trigger regions, wherein each of the confidence scores represents a level of certainty associated with an ability of a corresponding trigger region to accurately predict the bolus arrival within the volume of interest based on identification of the bolus within the corresponding trigger region; and acquiring a diagnostic scan of the volume of interest at the forecasted third bolus arrival time.

24. The computer system of claim 23, wherein monitoring the automatically established trigger regions for bolus arrival at the trigger regions includes performing motion compensation to correct for patient motion within the baseline image.

25. The computer system of claim 23, further comprising automatically identifying one or more anatomical landmarks within the baseline image and monitoring the automatically established trigger regions for bolus arrival at the trigger regions includes tracking the trigger regions and the anatomical landmarks and registering the trigger regions to an anatomical coordinate system referencing the tracked anatomical landmarks.

26. The computer system of claim 23, further comprising automatically assigning each of the trigger regions a confidence score.

* * * * *